(12) United States Patent
Warburton (10) Patent No.: US 6,338,266 B1
(45) Date of Patent: Jan. 15, 2002

(54) METHOD OF IDENTIFYING A GAS AND ASSOCIATED APPARATUS

(75) Inventor: P. Richard Warburton, Moon Township, PA (US)

(73) Assignee: Industrial Scientific Corporation, Oakdale, PA (US)

( * ) Notice: Subject to any disclaimer, the term of this patent is extended or adjusted under 35 U.S.C. 154(b) by 0 days.

(21) Appl. No.: 09/543,543

(22) Filed: Apr. 5, 2000

(51) Int. Cl.⁷ .................. G01N 27/404; G01N 27/30
(52) U.S. Cl. .............. 73/23.2; 73/1.02; 205/775; 205/783
(58) Field of Search .................. 73/1.02, 1.03, 73/1.04, 1.05, 1.06, 1.07, 23.2, 23.3, 64.47; 204/409, 415, 431; 205/782, 782.5, 783, 775, 779.5, 781, 786.5, 787, 793

(56) References Cited

U.S. PATENT DOCUMENTS

| 2,387,550 A | * | 10/1945 | Winkler .................. 73/23.2 |
| 3,429,784 A | * | 2/1969 | Molloy .................. 205/782.5 |
| 4,829,809 A | * | 5/1989 | Tantram et al. .......... 73/23.36 |
| 5,741,413 A | * | 4/1998 | Capetanopoulos .......... 205/783 |
| 5,885,844 A | * | 3/1999 | Weir et al. .............. 73/24.06 |
| 6,165,347 A | * | 12/2000 | Warburton .............. 205/782.5 |

FOREIGN PATENT DOCUMENTS

SU            1679367 A1  *  9/1991  ................. 73/1.02

* cited by examiner

Primary Examiner—Hezron Williams
Assistant Examiner—Michael Cygan
(74) Attorney, Agent, or Firm—Dennison, Scheiner, Schultz & Wakeman (57) ABSTRACT

A method for identifying an unknown gas using a diffusion limited sensor providing an electrical signal output when exposed to the gas. According to the method, a sensor is disposed in a chamber of fixed volume and having a gas input and gas output through which the gas flows, and the chamber is connected to a source of a known test gas of known concentration and known diffusion coefficient $D_k$. The input to the chamber is opened, causing the sensor to be exposed to the known test gas until a steady state electrical signal output from the sensor is obtained. The time $T_k$ necessary for the sensor to attain a predetermined percentage of the steady state output is determined. The chamber is then connected to a source of unknown gas, and the input is opened, and time $T_u$ necessary for the sensor to attain the predetermined percentage of a steady state output for the unknown gas is determined. The diffusion coefficient $D_u$ for the unknown gas is calculated by the formula $D_u = D_k \times (T_k/T_u)$; and the unknown gas is identified by its calculated diffusion coefficient.

15 Claims, 4 Drawing Sheets

METHOD OF IDENTIFYING A GAS AND ASSOCIATED APPARATUS

BACKGROUND OF THE INVENTION

1. Field of the Invention

This invention provides a method and related apparatus for identifying a component of gas mixture.

2. Description of Related Art

Potentially dangerous gas mixtures may be found in many work place environments. The dangers of these mixtures include the risk of fire or explosion from combustible gases, oxygen enrichment or deficiency and exposure to toxic gases. These dangers are well known and gas detection instruments are available to detect a wide range of gases, these instruments typically containing one or more gas sensors which give a proportional electrical response dependent upon the concentration of the gas to be detected. If the concentration exceeds allowed concentration limits, then the instrument will provide an alarm to warn nearby personnel, or it may activate other remedial actions, such as increasing the ventilation.

Gas detection instruments for safety applications are broadly divided into two groups. In the first group are portable instruments which are designed to be hand held or worn by the user and which provide personal monitoring. In the other group are fixed instruments, typically wall mounted, which provide area monitoring.

Combustible gases are often characterized by their lower explosive limit (LEL), which is the minimum concentration of that particular gas in air which can support combustion. If the concentration is below the LEL, then the gas will not burn without the continued support of an external ignition source. If the concentration of the gas is greater than the LEL, then once ignited, the combustible gas-air mixture will burn without the need for an external heat source. Indeed, many combustible gas-air mixtures will explode if ignited at concentrations greater than the LEL.

At very high concentrations of the combustible gas, there may be insufficient oxygen to support the combustion, and the combustible gas-air mixture will no longer burn. This upper concentration limit for flammability is known as the upper explosive limit (UEL). The upper and lower explosive limits depend on the gas to be detected, as may be seen from the data below, copied from the CRC Handbook of Chemistry and Physics, 68$^{th}$ Edition, 1987–1988, Publ. CRC Press, Boca Raton, Fla.

Limits of Flammability of Gases in Air

| Gas | LEL (% vol) | UEL (% vol) |
|---|---|---|
| Acetylene HCCH | 2.50 | 80.00 |
| Ammonia $NH_3$ | 15.5 | 27.0 |
| Benzene $C_6H_6$ | 1.40 | 7.10 |
| Hydrogen $H_2$ | 4.00 | 74.24 |
| Methane $CH_4$ | 5.00 | 15.00 |
| Pentane $C_5H_{12}$ | 1.40 | 7.80 |
| Xylene $C_6H_4(CH_3)_2$ | 1.00 | 6.00 |

There are three main types of sensors used to detect combustible gases. For general leak detection, metal oxide, especially tin oxide sensors are used. The electrical conductivity of the metal oxide changes when exposed to the combustible gas at high temperature.

Infrared sensors typically measure the absorption of the gas at 2940 cm$^{-1}$ (~3.4 μm), which corresponds to the carbon-hydrogen (C—H) bond stretching frequency. The absorption of the infrared radiation depends on the number of C—H bonds stretching in the molecule. One of the limitations of infrared detectors is that molecules such as carbon monoxide (CO) and hydrogen ($H_2$) do not have an absorbance at or near 3.4 μm bond, since they do not have any C—H bonds. Even molecules such as acetylene (HC≡CH) and benzene ($C_6H_6$) which both have C—H bonds often have low sensitivity at 3.4 μm since the triple bond in acetylene and the aromatic ring in benzene shift the absorbance of the C—H stretch from that observed for aliphatic hydrocarbons. These effects of molecular substitution on the C—H bond vibration frequency are well known, and can be found in standard texts such as D. H. Williams, I. Fleming, "Spectroscopic methods in Organic Chemistry", third edition, McGraw-Hill book Company, Ltd., London, 1980.

The other major type of sensor for combustible gas is the catalytic bead sensor, which measures the heat of combustion. The detector bead of a catalytic bead sensor comprises a small platinum coil encased in a ceramic bead, containing precious metal catalysts. The combustible gas enters the sensor and travels to the catalytic bead by natural diffusion. The gas is combusted at the bead surface, aided by the catalysts and the resulting release of heat raises the temperature of the bead. This rise in temperature results in an increase in resistance of the platinum coil, which is normally detected using a Wheatstone bridge. Within the sensor, there is usually a second bead, the reference or compensator bead, which is constructed similarly to the detector bead, but without the catalyst. The compensator bead comprises one of the other arms of the Wheatstone bridge, and it is used to cancel out any other non-combustion related responses of the beads, such as changes in ambient humidity or thermal conductivity of the gas.

The response of the catalytic bead depends primarily on the heat of combustion of the gas and the rate at which the gas can diffuse to the detector bead. Catalytic bead sensors are widely used for monitoring for combustible gases in the workplace due to their excellent precision and accuracy.

It is common practice to express the concentration of combustible gases as a percentage of the LEL, and thus 2.5% volume of methane is 50% LEL. The response of catalytic bead sensors is approximately linear over their useful range (0 to 100% LEL), and setting the empirically determined proportionality constant between the output response and the concentration is called calibration. However, for a catalytic bead sensor, the sensitivity to gas varies with the type of gas. For example, compared to a relative response to 50% LEL of methane of 1.0, the response to 50% LEL pentane is only about 0.5. A more thorough discussion of catalytic bead sensors may be found in the review by J. G. Firth, "Measurement of Flammable Gases and Vapors" in "C. F. Cullis, J. G. Firth (Eds.), "Detection and Measurement of Hazardous Gases", Heinemann, London, 1981.

Many of the commonly encountered toxic gases are detected using amperometric electrochemical gas sensors. A typical electrochemical sensor is usually constructed with two or more electrodes in contact with an electrolyte. The electrode is usually separated from the outside environment by a gas porous membrane, and other diffusion barriers. The gas to be detected enters the sensor and passes through the membrane to the working electrode, where is it either oxidized or reduced, or the rate of oxidation or reduction of the electrode or another species in an electrolyte may be limited the availability of the toxic gas. The resulting electrical current is proportional to the rate at which the gas is being consumed by the electrode. The output current is therefore usually linearly proportional to the gas concentration, since the response is limited by the rate at which the gas to be detected can diffuse into the sensor.

The nature of the response of the sensor to a toxic gas depends on both the design of the sensor and the nature of the gas. Some gases such as carbon monoxide (CO) and hydrogen ($H_2$) are oxidized at the electrode, whereas other gases such as chlorine and nitrogen dioxide are usually reduced at the sensor electrode. While the oxidation of carbon monoxide to carbon dioxide ($CO_2$) is a two-electron process, the oxidation of hydrogen sulfide ($H_2S$) to sulfuric acid ($H_2SO_4$) is an eight-electron process. Thus a diffusion limited sensor which responds to both hydrogen sulfide and carbon monoxide will give a stronger response to the hydrogen sulfide, for a given concentration of gas.

The above examples of sensor technology are intended to illustrate that the signal obtained for a combustible or toxic gas depends on both the sensor technology employed, and on the properties of the individual gases. This fact poses a quandary for personnel who risk being exposed to a variety of different gases. If they use a broad band sensor, i.e. a sensor that is sensitive to a wide variety of gas types, then there is the risk that the alarm levels will not be appropriate for any given gas. However, if they instead decide to use a sensor selective for a particular gas, then there is the risk that an unanticipated hazardous gas will not be detected at all. In addition, they may have to use instruments which contain many sensors or they may have to carry several instruments, which may be both expensive and cumbersome.

It is now common practice to use a broad band sensor for combustible gases, such as a sensor based on infrared or catalytic bead technology, and to set the alarm levels to match the gas with the least sensitive response. If there is likely to be either methane or pentane in a particular environment, then a catalytic sensor based instrument will usually be calibrated with pentane, since pentane has the lower sensitivity. However, this approach can result in false alarms since a safe concentration of methane will set the instrument into alarm. With a broad band sensor, such as the catalytic bead sensor, it is not currently possible to determine whether a response is coming from methane or pentane.

In contrast, toxic gases are usually detected with sensors specific to a particular gas. This difference between the combustible gases and the toxic gases is in part due to the wide variation in risk associated with a toxic gas. For example, carbon dioxide has an OSHA eight-hour permissible exposure limit (PEL) of 5000 ppm, carbon monoxide has a PEL of 50 ppm, sulfur dioxide has a PEL of 5 ppm and chlorine dioxide has a PEL of 0.1 ppm. Another reason for this difference is that it is often easier to fabricate an electrochemical sensor to be selective to a particular toxic gas, than to fabricate a catalytic bead sensor to be selective to a particular combustible gas. Some attempts have been made to produce broad band electrochemical gas sensors, but they also suffer from the drawback of deciding where to set the alarm levels. For example, a sensor which gives a response to both sulfur dioxide and carbon monoxide, corresponding to 10 ppm, is five times below the OSHA PEL for carbon monoxide but twice the OSHA PEL for sulfur dioxide, even though both gases are oxidized by two electrons.

Clearly, a method is required so that a gas detection instrument can both identify the gas, and select the appropriate alarm threshold level to be used.

Several ways have been developed to identify the components of a potentially hazardous atmosphere. Detector tubes kits are available, in which a series of colorimetric tubes are used, initially identifying the unknown gas by broad chemical classification (e.g. acidic, halogenated or reducing gas), followed by successive iterations until the gas is identified. However, this manual approach is time consuming and cumbersome, and provides the analysis only at a single moment in time ("Drager-Tube Handbook" $8^{th}$ Edition, National Draeger Inc, Pittsburgh, Pa.).

In the past, gases were identified by collecting a sample, either on an absorbent, such as activated charcoal, or in a clean gas chamber, followed by laboratory analysis. This method is time consuming, and since the analysis has to be performed elsewhere, there is often a considerable delay from the time the sample is taken to the time when the gas is identified.

Laboratory-based methods for gas identification usually involve large, expensive and typically immobile equipment, such as mass spectrometers, gas chromatographs and infrared spectrometers. Considerable effort has been made to adapt these laboratory instruments for use in the field and several manufacturers offer portable gas chromatographs (for example HNU Systems, Newton Mass. 02461 and Viking Instruments Corporation, Chantilly, Va. 20151). Mass spectrometers offer high sensitivity and good selectivity, and despite the difficulties of requiring a high vacuum and other engineering challenges, portable and semi-portable mass spectrometers have been developed by several companies. For example Foster-Monitor Group of Cheswick, Pa. has a mass spectrometer that can collect a sample and identify component gases, selected by their molecular masses. Both the portable mass spectrometers and gas chromatographs offer the capability of being able to encounter an unknown gas and to identify the gas so encountered. While these devices offer considerable potential, they remain too expensive for routine safety monitoring, and tend to be used for more specialized applications.

Infrared spectroscopy can also be used to identify a particular gas. Whereas most infrared combustible gas sensors operate at a single wavelength, and thus have difficulty distinguishing between various hydrocarbons, the full infrared spectra of most organic compounds are unique. Thus, if the full spectrum is obtained with an infrared spectrometer, then the spectrum can be compared against a library of infrared spectra. Due to the complexity of the optics, the cost associated with obtaining a full spectrum and the subsequent data analysis increases the cost of this instrument well beyond that normally used for routine safety monitoring.

Sensor arrays have been developed which are capable of identifying a wide range of gases. These sensor arrays effectively have a large number of sensor elements, each with a different response characteristic. The combined pattern of response from a sensor array can be used to indicate the concentration and identity of gaseous species present. However, sensor arrays have two drawbacks. The first drawback is that the pattern recognition requires a very complex mathematical analysis, and thus a significant computer analysis is required to achieve useful results. The second and more important drawback is that the present day sensor arrays do not have the accuracy and reliability necessary for safety applications, although it is likely that both of these problems will be overcome in the future. Sensors arrays are now commercially available, for example, from Cyrano Sciences Inc, Pasadena Calif., and are being used for applications such as food quality and wine classification. The operation of these sensor arrays has been described by M. S. Freund and N. S. Lewis in proceedings of the National Academy of Science (1995), 92, 2652–2656 and by N. S. Lewis in U.S. Pat. No. 5,571,401. Details of other sensor arrays can be found in the Proceedings of the 6th International Symposium of Olefaction and Electronic Nose (ISCEN99), held at Tuebingen, Germany, September 1999 (ISBN 3-00-004819-7).

As may be seen from the above discussion, there is a need for an economical method that will identify an unknown gas, so that the appropriate calibration and alarm set point values can be selected. The instrument should be economical enough to be incorporated in personnel and fixed-point safety monitoring equipment. Furthermore, the accuracy and precision of the gas concentration measurement should be as good as the present technology, and preferably the instrument should still use the existing sensor technologies, since they are well tested and have a good service record.

SUMMARY OF THE INVENTION

Accordingly, it is an object of the invention to provide a process for determining an unknown gas by determination of its diffusion coefficient.

It is a further object of this invention to use the measurement of the diffusion coefficient of an analyte component to determine whether a gas detection instrument is operating correctly.

It is a further object of the invention to determine the identity and concentration of gases in a gas mixture by measurement of the time dependent response of a sensor.

To achieve these and other objects, the invention utilizes the response time of a sensor to calculate the diffusion coefficient of an unknown gas.

More specifically, the diffusion coefficient of the analyte component within a gas mixture is calculated by comparison of the response time of the sensor to the response time of the sensor to a known reactive gas mixture. The response time is defined as the time necessary for the output signal to reach steady state after the application of the gas to the sensor. The calculated diffusion coefficient is then used to identify the analyte gas.

In a further embodiment of the invention, the response time is defined as the time necessary for the output signal to reach a fraction of the steady state after the application of an operating potential to the sensor.

In a further embodiment of this invention, the diffusion coefficient of a gas is calculated by comparison of the recovery time of the sensor exposed to the gas mixture after ceasing to supply the gas to the sensor or to a chamber containing the sensor. The recovery time is defined as the time necessary for the output signal of the sensor to reach a fraction, e.g. 10%, of the steady state signal in the presence of the gas.

In a still further embodiment of the invention, several response times (the time necessary to reach a given percentage of steady state signal) or several recovery times (the time necessary to reach a given percentage of base signal after reaching steady state) are measured and are used to identify one or more components of a gas mixture by comparison with response time or recovery time, respectively, of the sensor to a gas of known composition.

DESCRIPTION OF THE PREFERRED EMBODIMENTS

Figure 1:
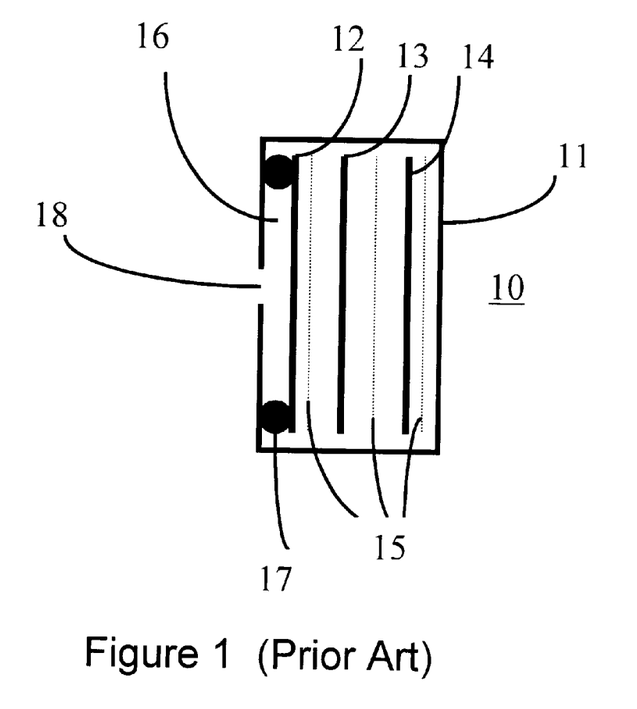
FIG. 1 is a schematic representation of a prior art electrochemical gas sensor.

The process of the invention may be performed using a typical prior art electrochemical sensor 10, as shown in FIG. 1, comprising a sensor body 11 containing three electrodes, a working electrode 12, a reference electrode 13 and a counter electrode 14. The three electrodes 12, 13, and 14 are separated by inert media 15, soaked in electrolyte. Typically this inert media 15 comprises glass paper, and the electrolyte may be an aqueous or non-aqueous solution of a salt or acid, to provide ionic electrical conductivity between the electrodes 12, 13 and 14. The electrolyte is retained within the sensor 10 by the compression of an O-ring seal 17 disposed between sensor body 11 and electrode 12. The gas to be detected diffuses into the sensor 10 through a gas entry hole 18 into a volume 16 within the sensor 10. The gas diffuses through the working electrode membrane 12, which typically comprises a porous membrane with a precious metal (not shown) fixed onto the inner surface of the membrane comprising electrode 12. The magnitude of the steady state response of most amperometric electrochemical gas sensors is limited by the rate at which the gas to be detected can diffuse into the sensor, and the sensors are designed to be limited by the rate of gas diffusion by making the gas entry hole 18 small enough that it presents a significant diffusion barrier to the gas. The advantages of making the sensor diffusion limited are that the response is linear with concentration and the sensitivity of the sensor (sensitivity= steady state response to the gas/gas concentration) becomes independent of small variations in electrode potentials, or small losses in electrode catalytic activity.

The operation of this electrochemical sensor has been described for illustrative purposes only and many variations on electrochemical sensor design are known in the prior art. Further details of electrochemical sensor operation and design may be found in the following references: S. C. Chang, J. R. Stetter, C. S. Cha, "Amperometric Gas Sensors", Talanta (1993), 40 (4) 461–477; B. S. Hobbs, A. D. S. Tantram, R. Chan-Henry in "Techniques and Mechanisms in Gas Sensing", Ed. P. T. Moseley, J. O. W. Norris and D. E. Williams, Adam Hilger, Bristol, 1991.

Figure 2:
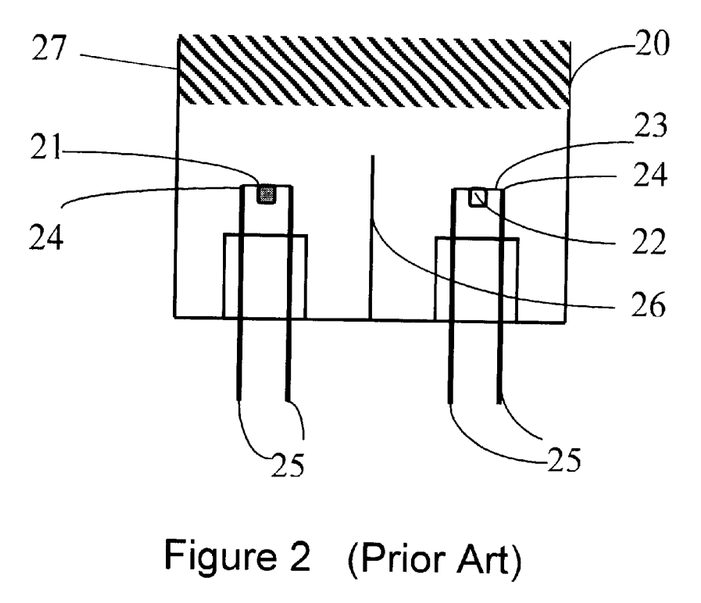
FIG. 2 is a schematic representation of a prior art catalytic bead gas sensor.

Alternatively, the invention may be carried out using a typical prior art catalytic bead sensor 20, as shown FIG. 2, comprising two beads, a detector bead 21 and a reference bead 22, each disposed on a wire coil 23 embedded in a alumina or other ceramic. The ends of this wire coil 23 are attached to posts 24 in such a way as to suspend the beads 21 and 22 between the posts 24. These posts 24 serve the dual role of mechanically supporting the beads 21 and 22, and also providing an electrical connection to external contacts 25. The two beads 21 are 22 are usually separated by a partition 26, which serves to reduce air currents within the sensor 20.

The detector bead 21 additionally has a precious metal catalyst (not shown) deposited on the surface of the bead 21, whereas the reference bead 22 does not. The beads 21 and 22 are held at a high temperature, >500° C. being typical, which in combination with the catalyst facilitates the combustion of any combustible gases which reach the detector bead 21. Since the reference bead 22 does not have the catalyst on its surface, no combustion occurs on the reference bead 22. The increase in temperature from the combustion of the combustible gas on the detector bead 21 results in an increase in the resistance of the wire coil inside the bead 21. This small increase in resistance is conveniently detected with a Wheatstone bridge circuit (not shown) connected to the contacts 25, and provides the output signal. Gas to be analyzed enters the sensor 20 by diffusing through a sintered metal disk 27, which serves the role of both a diffusion barrier and flame arrestor. Catalytic bead sensors are well known in the prior art, and details may be found in reference texts. (J. G. Firth, "Measurement of Flammable Gases and Vapors" in "C. F. Cullis, J. G. Firth (Eds.), "Detection and Measurement of Hazardous Gases", Publ. Heinemann, London, 1981).

In common practice, sensors for gas detection are typically operated by exposing the sensor to the ambient atmosphere and thus allowing gas to diffuse into the sensor. Alternatively, the gas detection instrument may include a pump which draws in the gas from the ambient atmosphere and then passes it over the sensor. The response of the sensor in an aspirated sample gas detection instrument will still be diffusion limited, since the rate at which the gas enters the sensor will still be limited by diffusion.

Figure 3:
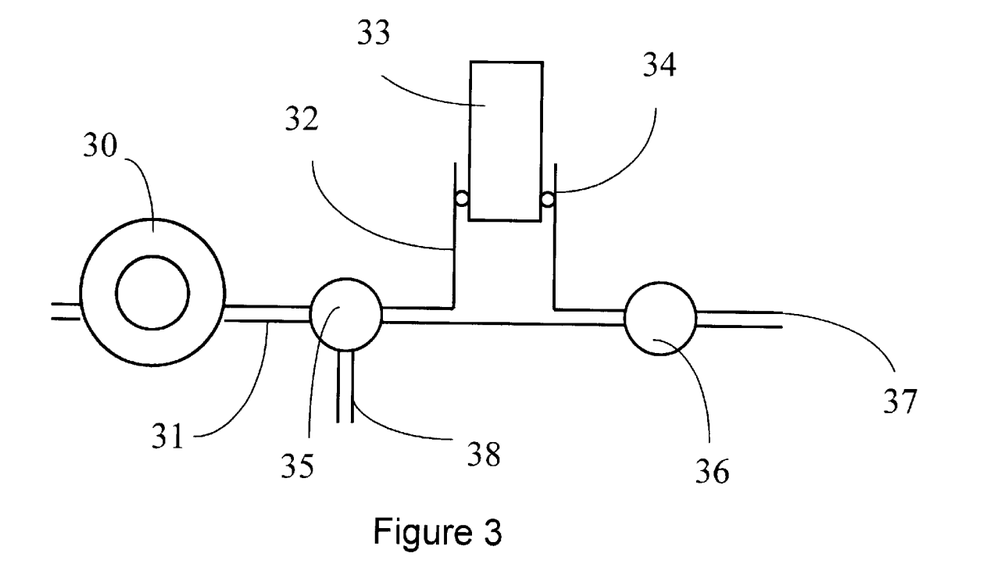
FIG. 3 is a schematic representation of a gas flow system incorporating a gas detection instrument, and adapted for practicing the invention.

FIG. 3 shows the gas flow system of a gas detection instrument. The gas is drawn in from the ambient atmosphere by a pump 30. The gas passes through tubing 31 to a two way valve 35. If the valve is activated, then the gas passes through the valve 35 into a sensor manifold 32, whereupon it can diffuse into sensor 33, which can be an electrochemical or catalytic bead sensor of the types discussed above, and give an output response. The sensor 33 makes an airtight seal with the sensor manifold 32 by means of an O-ring seal 34. The gas passes out of the sensor manifold 32 via a valve 36 to an exhaust 37. Valve 36 is open whenever valve 35 is activated and valve 36 is closed whenever valve 35 is not activated. When valve 35 is not activated, the gas from pump 30 is passed to an exhaust 38.

A steady state signal from sensor 33 is obtained by having valves 35 and 36 both open. The operation of the valves 35 and 36 is performed by a microprocessor or other controller as is known in the art (not shown).

According to the invention, the diffusion coefficient of the analyte gas can be calculated based on the response time of the sensor to the gas, and this determination of the diffusion coefficient D can be used to identify the gas. While in principle, the diffusion path parameters can be measured, thus allowing the direct calculation of the gas diffusion coefficient, it is much more convenient to measure the gas diffusion coefficient relative to a calibration gas. The gas detection instrument is thus exposed to gas of known composition and known diffusion coefficient, which provides a calibration of the system. Then, comparison of the ratio of response time of the sensor upon exposure to an unknown gas to that of a known gas can be used to measure the diffusion coefficient of that gas and thus provide identification of the unknown gas.

The diffusion coefficient of a gas depends on the molecular weight of both the component gas and the balance gas, and on the molecular size. Therefore, two similarly sized molecules, for example ethylene ($CH_2=CH_2$) and ethane ($CH_3-CH_3$) are likely to have similar diffusion coefficients, and it would therefore be difficult to distinguish between them using this method. Similarly, the two toxic gases nitric oxide (NO) and carbon monoxide (CO) will have similar diffusion coefficients, and so it would also be difficult to distinguish between them using their diffusion coefficients. However, two dissimilar gases, such as methane ($CH_4$) and pentane ($C_5H_{12}$), or carbon monoxide and sulfur dioxide ($SO_2$) will have very different diffusion coefficients, and thus can be more readily distinguished. The ability to distinguish between two different gases will depend on the magnitude of their relative diffusion coefficients and the experimental error in the measurement of the diffusion coefficients.

Once the gas diffusion coefficient has been measured, the gas can be identified by comparison of the diffusion coefficient with values for known gases. When the gas has been identified, the correct sensitivity parameters and alarm threshold limits can be used by the gas detection instrument. Most modern gas detection instruments contain a microprocessor or other controller with associated memory or equivalent device, and it is relatively easy for a gas detection instrument to do the requisite calculations and to access 'look-up' tables or other information storage means within the instrument to compare measured with expected diffusion coefficients and to obtain the sensitivity parameters and the alarm threshold limits.

Figure 4:
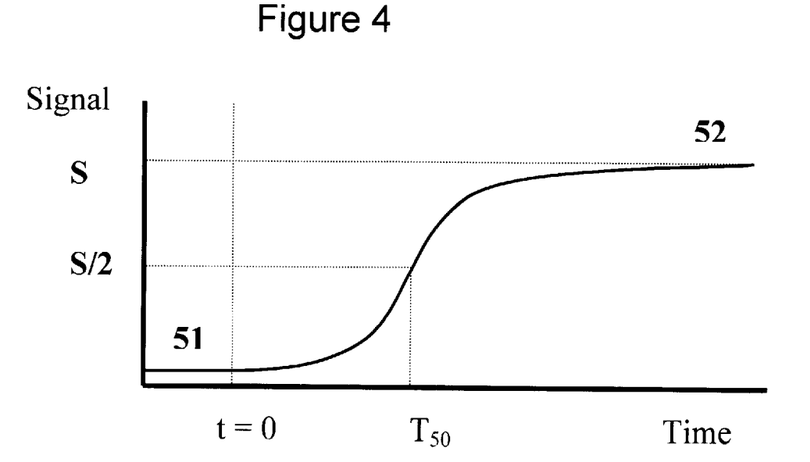
FIG. 4 is a graph showing the response of a sensor to a gas over a period of time.

In one embodiment of this invention, the diffusion coefficient can be determined by measuring the response time of a diffusion-limited sensor, upon applying gas to the sensor. A representation of the response of a sensor to a gas is shown in FIG. 4. Prior to the activation of the valve, none of the gas reaches the sensor and so the output is essentially zero, as indicated at point 51. When the valve is activated (t=0), the gas diffuses into the sensor and the output rises to an eventual steady state S, shown at point 52. The response time of a sensor may be described by a $T_{50}$, which is the time taken for the sensor to reach fifty percent of its steady state output signal (S/2) after activation of the valve. Other response times, such as $T_{90}$=time to ninety percent of steady state value, can be similarly defined. Since the response time is limited by the diffusion of the gas into the sensor, the response time, e.g. $T_{50}$, will depend on the diffusion coefficient of the gas. Thus, the response time can be used to provide a measure of the diffusion coefficient. The most convenient method to implement this embodiment of the invention is to measure the response time of the sensor to a known gas mixture, i.e. to calibrate the response characteristics, and to then to compare the response time of other gases to the response of this calibration gas.

If the response time of the sensor is determined solely by gas diffusion, then Fick's second law of diffusion can describe the response. Fick's second law of diffusion can be expressed for one dimension by the following partial differential equation:

$$dC/dt = D d^2C/dx^2$$

wherein C is the concentration, t is time, D is the gas diffusion coefficient and x is distance. This equation can be solved analytically by standard methods, but it is more convenient to solve it numerically. Fick's second law can be expressed in finite difference form as follows:

$$C(x,t+\Delta) = C(x,t) + (D\Delta t/\Delta x^2)[C(x+\Delta x,t) - 2C(x,t) + C(x-\Delta x,t)]$$

where $C(x,t)$ defines the concentration a point x, and time t, $t+\Delta t$ represents the next increment in time, and the $x+\Delta x$ and x−Δx represents the next and former increment in distance respectively. The numerical solution can readily be obtained by use of a conventional spread sheet program run on a personal computer. Further details of this approach to solving diffusion problems may be found in the appendix of A. J. Bard, L. R. Faulkner, *Electrochemical Methods, Fundamentals and Applications,* Publ. John Wiley & Sons, New York, 1980.

A simple model was used to simulate a gas sensor in order to identify the key relationships between the diffusion coefficient of the gas and the response time. The model included a diffusion path, which was one cm long, one cm in cross sectional area and at the end of the diffusion barrier there was a planar detector element, across the entire cross section of the diffusion path. This detector element consumed all of the gas, which reached it, i.e. the gas concentration at the detector element was held at zero (C=0 at x=0). At the open end of the sensor, the gas concentration was stepped from an initial zero concentration to the bulk concentration of the gas. For a diffusion limited sensor, such as a catalytic bead sensor or an amperometric electrochemical sensor, the response is proportional to the flux of gas to the detector element (the catalytic bead or electrode respectively). The flux of gas $\phi$ reaching the detector element in the model, and thus the output signal, was calculated based on the concentration of the gas at one distance increment from the detection element, multiplied by the gas diffusion coefficient and divided by the distance increment $$\phi = D(C_o, \Delta x)\Delta x$$

This equation is an expression of Fick's First law of diffusion, which was used to calculate the steady state flux of gas $\phi$ to the detection element, where $C_o$ is the bulk concentration and X is the total distance along the diffusion path.

$$\phi_{ss} = D\ C/X$$

At long times, the flux calculated from the numerical fit to Fick's second law of diffusion was found to converge with the steady state flux calculated using Fick's first law of diffusion, as expected.

The time taken for the flux reaching the detector element to reach 10%, 25%, 50% or 90% of the steady state value, after applying gas to the sensor was calculated to give the $T_{10}$, $T_{25}$, $T_{50}$ and $T_{90}$ response times respectively.

Figure 5:
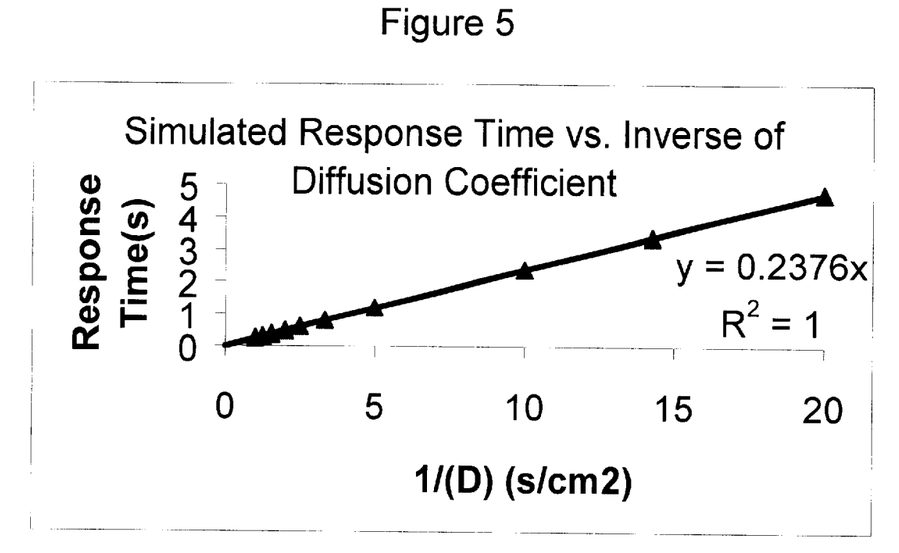
FIG. 5 is a graph showing the theoretical relationship between response time and diffusion coefficient, calculated from a numerical solution to Fick's second law of diffusion.

The response times were found to be independent of gas concentration, but inversely proportional to the diffusion coefficient of the gas. FIG. 5 shows a graph of calculated response time ($T_{50}$) as a function of the inverse of the gas diffusion coefficient. A linear fit of this calculated data passed through the origin and had a correlation coefficient of 1.00. Straight lines, which passed through the origin, were also obtained for $T_{10}$ and $T_{90}$ response times, but with larger and smaller slopes respectively. Thus, this model clearly predicts that response time of the sensor is inversely proportional to the gas diffusion coefficient.

In principle, it is possible to calculate the response time for a real sensor if the diffusion properties of the sensor are known (for example see P. R. Warburton, M. P. Pagano, R. Hoover, M. Logman, K. Crytzer, Y. J. Warburton, *Analytical Chemistry,* (1998), 70, 998). However, this calculation is often not practical because sensors often have multiple and poorly defined diffusion barriers. Instead of calculating the diffusion path, the more common procedure is to calibrate the sensor by empirically matching the output signal from the sensor to a known value, by exposing the sensor to a gas of known composition. Therefore, if the sensor is exposed to a calibration gas or known concentration, and the response time and steady state signal are measured, then the empirical calibration constant relating the response time of the sensor (e.g. $T_{50}$ or $T_{90}$) to the gas diffusion coefficient can be found.

The empirical calibration constant relating the gas concentration to the steady state signal can also be found. For an electrochemical sensor, the steady state response $I_{ss}$ is given by the following well-known equation relating the response to the flux of gas reaching the electrode $\phi_{ss}$, the number of electrons n, and Faraday's constant (F=9.648×10$^4$ C/mol).

$$I_{ss} = nF\phi_{ss}$$

Similarly, the steady state response $S_{ss}$ of a catalytic bead sensor is given by the following equation:

$$S_{ss} = KH\phi_{ss}$$

where H is a gas specific response constant and K is a constant of the sensor. For both types of sensors, and diffusion limited sensors in general, the steady state response depends on the gas concentration, a gas specific constant, and a sensor/instrument specific constant.

Steady state Response=(Gas Constant)×(Instrument Constant)× (Gas Concentration)

The gas specific constants are known for many types of gases, or easily measured, by comparing the response of the diffusion limited sensor to the new gas to that of a reference gas. For example, a broad band electrochemical gas detection instrument may be calibrated with carbon monoxide, such that the output display reads 50 ppm CO when this concentration of gas is applied to the instrument. When a mixture containing 50 ppm hydrogen sulfide is applied to the sensor, the instrument will typically read about 200 ppm CO, if the sensor response is diffusion limited to both carbon monoxide and hydrogen sulfide. In this case the gas specific constant for hydrogen sulfide is four times that of carbon monoxide. This arises because the oxidation of carbon monoxide is a two-electron process, whereas the oxidation of hydrogen sulfide is an eight-electron process. Similarly, if an instrument containing a catalytic bead sensor is calibrated with 2.5% v/v LEL methane in air, it may read 50% LEL. However, if this instrument is then exposed to 50% LEL pentane (0.70% v/v) in air, it will only read about 25% LEL. Thus the gas specific response constant of most catalytic bead sensors to pentane is only about half than for methane, for the response of both gases displayed as % LEL.

In applicant's earlier U.S. application Ser. No. 09/310, 330, filed on May 12, 1999, now U.S. Pat. No. 6,165,347, a method was disclosed to identify the reactive component for a gas mixture by its diffusion coefficient. In this application the diffusion coefficient was calculated from the ratio of the steady state signal from a diffusion limited sensor and the integrated signal from the same sensor as it consumed the gas within a small volume. For example, using the apparatus shown in FIG. 6, the steady state response of the sensor 70 was measured with valve 73 open. On closing valve 73, the output from the sensor 70 decreased as the gas in volume 77 was consumed by the sensor 70. It was shown in this application, that the ratio of the steady state current to the integrated signal from the sensor 70 upon closure of valve 73 response was proportional to the diffusion coefficient of the analyte gas.

Figure 6:
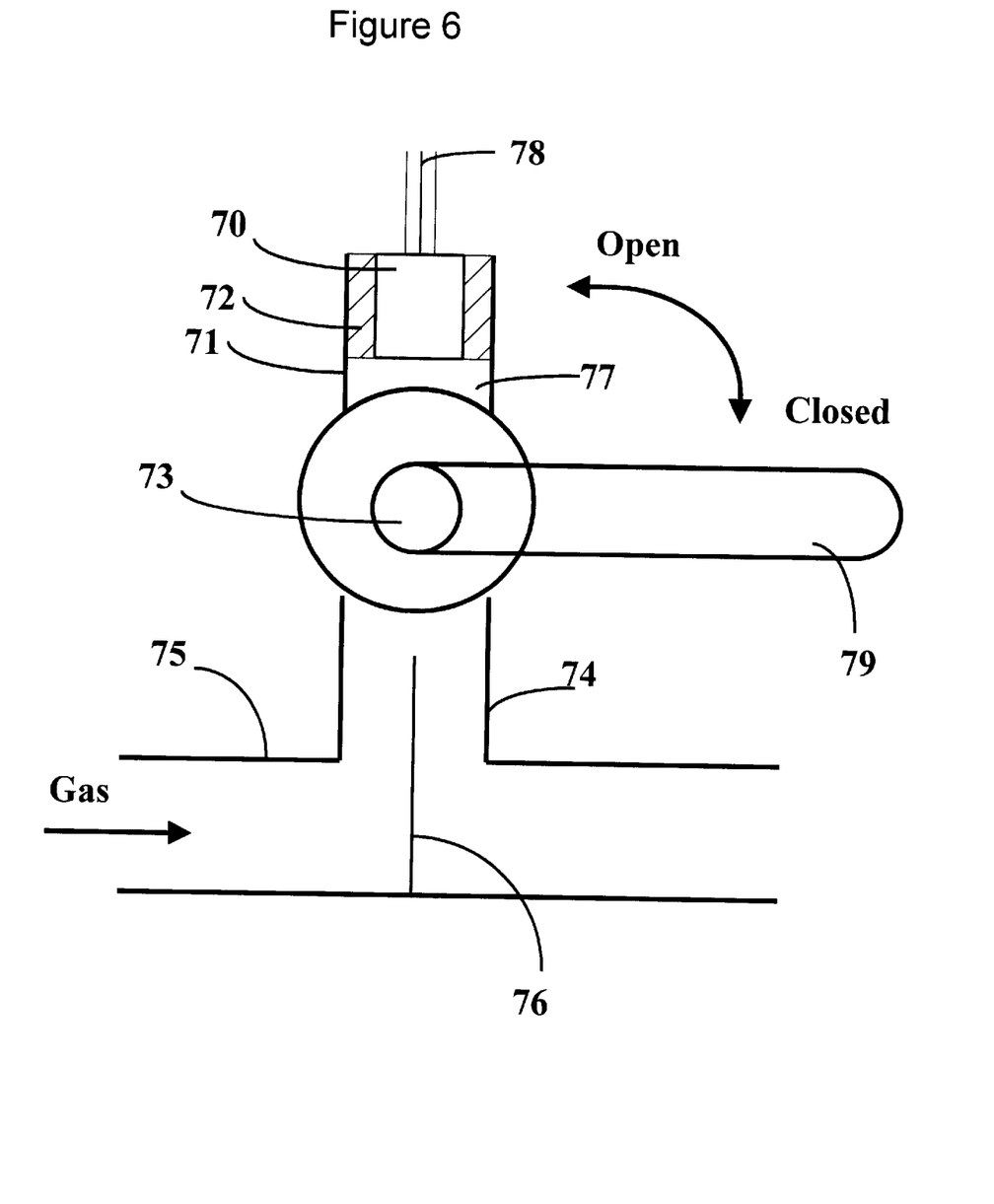
FIG. 6 is a representation of an apparatus used in U.S. application Ser. No. 09/310,330 to determine signal decay with a fixed volume of gas.

In a further embodiment of this invention it has since been determined that the time constant of the signal decay is inversely proportional to the diffusion coefficient of the analyte gas. The following model readily explains this result, as is illustrated using the apparatus shown in FIG. 6. Consider the small chamber 77, defined by the sensor 70, sealant 72, tube 71 and ball valve 73. This chamber 77 can be filled with gas by opening the ball valve 73, while gas is flowing through tube 75. In most sensors, there is a diffusion barrier, for example opening 18 in FIG. 1, or the sinter 27 in FIG. 2, which restricts the flow of gas into the sensor. In contrast, the movement of gas within the chamber 77 in FIG. 5 is unrestricted. Therefore, it can be assumed that the gas within chamber 77 remains essentially of uniform composition, since the natural movement of the gas within chamber 77, by diffusion or turbulent flow, will tend to even out any concentration differences. The flux ($\psi$) of gas into the sensor is given by the following equation:

$$\psi = C\Delta D$$

where C is the gas concentration in the chamber 77, $\Delta$ represents the diffusion barrier the gas must pass through to enter the sensor and D is the gas diffusion coefficient. Since the sensor is consuming the gas, the concentration of gas C in the chamber 77 decreases with time, once the valve 73 is closed. The total amount of gas N (in moles) is given by the product of the concentration of gas C and the volume of chamber 77 V. The consumption of gas can be written as follows:

$$dN/dt = \psi = C\Delta D$$

Since C=N/V, the expression becomes:

$$dN/dt = N\Delta D/V$$

which upon integration, gives a simple exponential decay, where $N_o$ is the amount of gas in chamber 77 at the start of the experiment, when the valve 73 is closed:

$$N = N_o \exp(-\Delta Dt/V)$$

Or equivalently:

$$C = C_o \exp(-\Delta Dt/V)$$

where $C_o$ is the concentration of gas in chamber 77 at the start of the experiment, when the valve 73 is closed. Thus upon closing the valve 73, the concentration of the gas within the chamber 77 is expected to decrease with an exponential decay, and hence the output from the sensor is also expected to show a similar form.

The time for the decay to reach half of its initial value ($T_{50r}$, half life) is readily calculated:

$$T_{50r} = 0.693 V/(\Delta D)$$

And similarly, the decay time for the sensor output signal to decay to 90% of its initial value ($T_{90r}$) after the valve 73 was closed is readily found:

$$T_{90r} = 2.303 V/(\Delta D)$$

Note that the decay time of the sensor comprises two parts, a constant of the apparatus ($V/\Delta$), and the gas diffusion coefficient D. Thus the decay time is inversely proportional to the gas diffusion coefficient.

In principle, it is possible to measure the values of the chamber volume V, and the diffusion characteristics of the sensor gas path $\Delta$. However, in practice it is more convenient to calibrate the apparatus with a known gas, of known gas diffusion coefficient and then to measure the diffusion coefficients of unknown gases with respect to the calibration gas.

Tantram and Gilbey in U.S. Pat. No. 4,829,809 described a method for calculating the concentration of gas using an apparatus similar to that shown in FIG. 6 using an electrochemical gas sensor. In their method, the chamber was flushed with gas, and then the chamber sealed. The output current from the sensor was monitored and the total charge passed (integrated signal–time curve) was calculated. By knowing the stoichiometry of the electrochemical reaction of the gas, and the volume of the chamber, the concentration of the gas could be found based on Faraday's law. In a similar method disclosed by Capetanopoulos in U.S. Pat. No. 5,741,413, instead of completely sealing off the gas chamber, the diffusion barrier in front of the sensor was changed. The steady state output from the sensor decayed to a new level as the gas concentration within a chamber between this additional diffusion barrier and the sensor decreased to a new steady state value. By integrating the curve resulting from the readjustment of the steady state, the concentration of the gas was calculated in an analogous manner to that used by Tantram.

The method described herein is quite different. Instead of integrating the area under a curve, or estimating this integral, as was done by both Tantram and Capetanopoulos, a simpler measurement of the response time is performed. Furthermore, the methods of both Tantram and Capetanopoulos are limited to measuring the concentration of a known gas, whereas in this method described herein, it is possible to identify an unknown gas, and then to measure its concentration.

In another embodiment of this invention, the response time of a sensor upon applying power to a sensor in the presence of a reactive gas (i.e. a gas to which the sensor produces a response) can be used to identify the gas. Consider a sensor, such as a catalytic bead sensor which is initially not under power, and thus any combustible gas present within the sensor is not consumed. If the sensor is designed such that the time required for the sensor to reach steady state temperature is fast compared to the rates of gas diffusion, then applying power to the sensor will rapidly cause the bead to reach its operating temperature. Subsequently, any combustible gas which reaches the detector bead will be consumed, producing the output signal. The gas concentration at the bead surface will rapidly be reduced to essentially zero, and thus a region of lower gas concentration will be established in the air near the surface of the bead. This depletion layer will extend into the ambient gas, until limited by the natural turbulence of the gas. Once this steady state limitation on the depletion layer is reached, the flux of gas reaching the sensor approaches the steady state response.

This approach can be described mathematically by solving Fick's second law of diffusion. The mathematical solution to this problem is well known for electrochemical systems, and for example, for linear diffusion in one dimension, the solution which is known as the Cottrell equation is:

$$I = nF\Delta D^{1/2}C_o/(\pi^{1/2}t^{1/2})$$

where I is the current, n is the number of electrons, F is the Faraday constant, $\Delta$ is a value for the sensor diffusion path, D is the gas diffusion coefficient, $C_o$ is the bulk gas concentration, and t is the time from applying the operating potential to the sensor electrode. Derivations of this equation may be found in standard texts such as "Instrumental Methods in Electrochemistry", by the Southampton Electrochemical Group, Publ. Ellis Horwood Ltd., Chichester, 1985.

For a catalytic bead sensor, the directly analogous equation is:

$$S = KH\Delta D^{1/2} C_o / (\pi^{1/2} t^{1/2})$$

where S is the output signal, H is a gas specific response constant, K is a constant of the sensor and the other terms are as previously defined.

From the equations for both the electrochemical sensors and for the catalytic bead sensors, it can be seen that whereas the steady state signal is proportional to the diffusion coefficient of the gas, the transient signal is proportional to the square root of the gas diffusion coefficient. Therefore, if the response time of the sensor on applying power to the bead, or potential to the working electrode, for catalytic bead and electrochemical sensors respectively, is compared to the steady state current, this ratio will be proportional to the square root of the diffusion coefficient. A plot of the response signal versus the inverse square root of the times since applying power will be a straight line. For an electrochemical sensor the slope is described by the following relationship:

$$\text{Slope} = nF \Delta D^{1/2} C_o / (\pi^{1/2})$$

For a catalytic bead sensor, the analogous relationship can be written, with all the terms as previously defined.

$$\text{Slope} = KH \Delta D^{1/2} C_o / (\pi^{1/2})$$

Thus, if both the slope and the steady state response are measured, the diffusion coefficient of the gas can be found. For an electrochemical sensor the ratio of the slope to the steady state current is given by:

$$\text{Steady state current/slope} = [nFCo\Delta D]/[nF\Delta D^{1/2} C_o / (\pi^{1/2})] = D^{1/2} / \pi^{1/2}$$

Thus the gas diffusion coefficient can easily be found:

$$D = \pi (\text{Steady state current})^2 / (\text{slope})^2$$

This embodiment of the invention has some distinct advantages, but it also has its limitations. Since the diffusion coefficient is calculated from the ratio of the steady state current to the slope from the response transient, an external reference of calibration standard is not needed.

Unfortunately, this embodiment of the invention will have limited applicability to electrochemical gas sensors. Most toxic gas sensors use high surface area porous electrodes, which tend to have a large pseudo-capacitance associated with them. On applying power, to the sensor, the current needed to change the potential of the electrodes is often large and thus the transient signal may not be due solely to the diffusion limited gas response. (P. R. Warburton, M. P. Pagano, R. Hoover, M. Logman, K. Crytzer, Y. J. Warburton, *Analytical Chemistry* (1998), 70, 998). This method will probably only have applicability to those sensors which use small solid electrodes. This embodiment also has limitations for use with combustible gas sensors. Many catalytic bead sensors require several seconds to thermally equilibrate upon application of power. A typical diffusion limited response time is on the order of one to two seconds, so the net response transient is a combination of effects, and is not simply diffusion controlled. However, current trends in catalytic bead sensors are towards smaller, lower power, faster response time catalytic bead sensors, and for these sensors this embodiment of the invention will be of great utility, and it is a simple matter for anyone experienced in the art of gas sensors to determine whether this embodiment can be applied for their application.

In a further embodiment of this invention, if the identity of the test gas is known, and the sensor response is limited by diffusion, then if the calculated gas diffusion coefficient obtained using any of the embodiments described above is close to the expected value, the sensor is deemed to be operating under diffusion control. However, if the measured diffusion coefficient differs greatly from the expected value of the diffusion coefficient, then there is a problem with either the instrument, the gas delivery system (e.g. blocked tubing), or with the sensor. Thus, this method can also be used to ascertain the functional status of the sensor and instrument.

In another embodiment of the invention, the sensor dynamic response to a gas mixture can be used to identify and quantify a mixture of reactive gases. The dynamic response refers to either the increase in signal on applying gas to the sensor, or the decrease in signal on ceasing to supply gas to the sensor. The concepts behind this embodiment of the invention can be easily illustrated by considering the sensor apparatus shown in FIG. 6. When the valve 73 is closed, the sensor 70 is exposed only to a small volume of gas 77 defined by the sensor 70, the tubing 71 and the valve 73. As discussed above, if movement of the gas inside the enclosed volume 77 is unrestricted, then the response from the sensor is limited by the rate of diffusion of the gas into the sensor 70. The output current from a diffusion-limited sensor is proportional to the flux of gas reaching the detector element of a sensor (e.g. the electrode 12 for an electrochemical sensor as shown in FIG. 1, or the catalytic bead 21 for a catalytic bead sensor shown in FIG. 2). Furthermore, the flux of gas depends on the concentration of gas to which the sensor 70 is exposed, and thus if the gas contains only one active component, then the output signal from the sensor 70 on closing the valve 73 will follow an exponential decay. The mathematical expression for this decay was derived above.

If the gas contains two active components, then the output from the sensor 70 will be the sum of the responses from the two gaseous components. The response to each component gas will be a simple exponential, and if the diffusion coefficients of the two gases are different, then the decay curve from the sensor can be described by the sum of the two exponential terms, one for each component gas respectively. Thus, for a gas mixture containing two active components, A and B, the response will be described by:

$$\text{Sensor Response} = C_A K_A \exp(-m_A t) + C_B K_B \exp(-m_B t)$$

where t is time, $C_A$ and $C_B$ represent the concentrations of gas components A and B, $K_A$ and $K_B$ are constants representing the gas response of the sensor to gases A and B, and $m_A$ and $m_B$ are the response factors for gases A and B respectively. By comparison to the derivation of the response to a single component above, the response factor $m_A$ and $m_B$ are equal to $\Delta/(VD_A)$ and $\Delta/(VD_B)$, wherein $D_A$ and $D_B$ are the diffusion coefficients of components A and B respectively.

If the sensor decay curve is fitted to a double exponential equation of the form:

$$\text{Sensor response} = W\exp(-Xt) + Y\exp(-Zt)$$

W, X, Y and Z are constants which are determined by the fit. Values for $m_A$ and $m_B$ can equated from X and Z.

Since the term Δ/V represents variables of the apparatus, which are independent of the gas, $m_A$ and $m_B$ are therefore inversely proportional to the diffusion coefficient of the gas. Methods to fit curves to known mathematical functions are well known in the art, for example the double exponential fit of the types described here can be obtained using commercial software packages such as Kaleidograph 3.0, from Synergy Software, Reading Pa. 19606.

The gases A and B can then be identified, based on the diffusion coefficient as described above. Once the gases A and B have been identified, the sensor response constants $K_a$ and $K_b$ can be readily obtained, since these values are well known for many of the common gases and they are also easily determined experimentally. Finally, the concentration of the gas components A and B can be found by dividing the mathematically obtained parameters W and Y by the respective response constant.

$$C_A = W/K_A \text{ and } C_B = Y/K_B$$

This method can be applied to more complex mixtures with greater numbers of active components. However, as the number of components increase, the accuracy of the mathematical fit decreases.

Using this embodiment of the invention it is possible to identify multiple active components of a test gas and determine their concentrations. In the description above, the invention was illustrated by the decay of the output signal from sensor 70 in FIG. 5, on closing valve 73. This experimental design was selected because it provides a simple decay curve, e.g. a double exponential for two active components of the test gas. Other configurations may give more complex decay curves. Further more, the method can also be applied to the increasing signal on applying gas to the sensor. The increasing signal though is typically a more complex function than a double exponential. In these circumstances, the mathematical form of the curve (either rise or decay) will depend greatly on the geometry of the gas flow/diffusion path. Even if the mathematical form of the curve is a more complex function, the output from the sensor can be approximated by the sum of the individual responses of the reactive component gases. Therefore, if the mathematical form of the curve is known or can be determined empirically (e.g. polynomial or other known described herein. The optimum equation and method of applying this invention will depend greatly on the gas path and other experimental parameters and can be determined for each case by those experienced in the art of gas sensor diffusion.

It will be useful for the instrument to be able to determine whether the gas mixture contains only a single active component or if it contains more than one active component. A relatively simple method that can be employed to first test whether the gas supplied to the sensor contains only a single active component or several active components is as follows. The sensor response or decay curve is obtained for a known gas, and several response times are measured. For example, the time for the sensor output to change by 10%, 25%, 50% and 75% is determined. This measurement with the known gas acts as a calibration. As described above, the response and decay time is a function of the gas diffusion coefficient. If the gas mixture contains two active components, one which has a lower diffusion coefficient and one with a higher diffusion coefficient than the calibration gas, then the response to the high diffusion coefficient gas will be faster than the response to the gas with the large diffusion coefficient. Assuming that the response or decay of the sensor is limited by the rate of diffusion of the active gases into the sensor, then the overall resulting response or recovery curves will be the supposition of the response curves of the individual components. The response of the sensor to the low diffusion coefficient gas will predominantly impact the shorter response and recovery times (e.g. $T_{10}$), and the response of the sensor to the high diffusion coefficient gas will predominately impact the longer response and recovery times (e.g. $T_{90}$).

The response curve for an unknown gas mixture is measured, and the response times at 10%, 25%, 50% and 75% are again measured, and compared to the reference. If the ratio of the response time for the unknown to the calibration gas is constant for all the response times, then the unknown gas contains only a single component. Conversely, if the ratio response times for the unknown gas mixture to the calibration gas mixture vary from short response times (e.g. $T_{10}$) to longer response times ($T_{75}$), then the gas mixture contains more than one active component.

If the response time of the unknown gas is faster than the calibration gas, then the active gas contains a component with a smaller diffusion coefficient than the calibration gas. Similarly, if the response time of the unknown gas is slower than the calibration gas, then the active gas contains a component with a larger diffusion coefficient than the calibration gas. Thus, comparison of the response curves of the unknown gas mixture to a calibration gas can be used to both determine the number of active components and to identify the active components.

Using the various methods of the invention, a known control gas is tested first, followed by testing of an unknown gas or gas mixture. The testing of the known and unknown gases need not be immediately sequential however; testing of the unknown gas may occur at some later time, with the determination relying on control parameters obtained earlier. Similarly, the unknown gas may be tested first, followed by testing of the control.

While this invention has been described for electrochemical and catalytic bead sensors, it is readily apparent that the same invention may be applied to any kind of sensor whose response is limited by the diffusion rate of the analyte species.

EXAMPLE 1

A simple apparatus, shown in FIG. 6, was constructed to demonstrate the practical utility of this invention. A catalytic bead sensor 70 from City Technology, Portsmouth, England, model 4P-100, was sealed into a short length of tubing 71 with a gas tight sealant 72 behind a three quarter-inch diameter ball valve 73. The ball valve 73 is connected via a short length of tubing 74 to a T connection to a tube 75 through which the test gas flows. A small baffle 76 was inserted into the tube 74 to promote the flow of gas towards the ball valve 73 and sensor 70. When the ball valve 73 is open, the test gas flows towards the sensor 70. When the ball valve 73 is closed, the flowing gas is prevented from reaching the sensor 70, and the sensor is exposed only to the gas in the sealed volume 77 determined by the sensor 70, sealant 72, tubing 71 and the ball valve 73. The sensor 70 was connected to a conventional Wheatstone bridge detection circuit (not shown) via leads 78, and the output signal was collected on an automated data acquisition system (also not shown). With the ball valve 73 closed, the sensor 70 was isolated from the test gas. After the test gas had flowed through the test equipment for several minutes, the ball valve 73 was opened using handle 79, and the output from the sensor 70 was followed with time as it rose to the steady state output. The response time ($T_{90}$) of the sensor was then determined. The $T_{90}$ is the time taken from when the valve 73 was opened to the time when the output from the sensor 70 reached ninety percent of its steady state response.

The apparatus was calibrated using 40% methane in air from a compressed gas cylinder. The response time for methane was calculated, and found to be $T_{90}$=15.6 seconds (average of four measurements).

The experiment was repeated with another test gas, test gas A, which contained a hydrocarbon gas in air. For test gas A, the $T_{90}$ response time was 33 seconds (average of three measurements). The relative diffusion coefficient of hydrocarbon in test gas A (relative to methane) may be found from the following relationship:

Relative Diffusion Coefficient=($T_{90}$ for Methane)/($T_{90}$ for Unknown Gas)

Thus, the relative diffusion coefficient of test gas A compared to methane is 0.47. Known values of the relative diffusion coefficients relative to the calibration gas methane, are shown below. Experimental values of the diffusion coefficient have been tabulated for many gases in the literature, or they can be calculated using standard methods (G. O. Nelson, "Gas Mixtures, Preparation and Control", Lewis Publishers, Boca Raton, Fla. 1992; E. L. Cussler "Diffusion, Mass Transfer in Fluid Systems", Cambridge University Press, Cambridge, 1992).

| GAS | Relative Diffusion Coefficient |
| --- | --- |
| Hydrogen | 3.32 |
| Methane | 1.0 (fixed) |
| Butane | 0.49 |
| Pentane | 0.39 |

Thus by comparison of the response time for test gas A to the ratio response time for methane, with the relative diffusion coefficients in the table, test gas A is identified as butane.

The cross sensitivity is defined as the signal produced per unit of gas concentration of one gas, relative to standard gas. For combustible gases, the concentration is often expressed as a percentage of the lower explosive limit. For the sensor 70 used in this example, a 4P-100 Cipel from City Technology Ltd., Portsmouth, United Kingdom, the nominal cross sensitivities relative to methane (=100%) are tabulated, and butane=65% (Product Data Handbook, vol. 1, Safety, issue 4.0, January 1997, City Technology Ltd., Portsmouth, United Kingdom).

Having identified test gas A as butane, the concentrations can be found from the steady state signal. The steady state output of the sensor exposed to 40% LEL methane in air was 45.4 mV. The steady state signal of the sensor exposed to test gas A was 15.9 mV, and since the cross sensitivity ratio for butane is 65%, the concentration of butane in test gas A is estimated to be 22% LEL butane.

Test gas B was 0.473% volume (25% LEL) butane in air from a compressed gas cylinder. This example has thus demonstrated that the method described in this disclosure can be used to both identify an unknown gas, and to estimate the concentration of the gas. These results clearly demonstrate the utility of this method.

EXAMPLE 2

Using the same experimental setup described in Example 1 and shown in FIG. 6, the identity of a gas was measured via the second embodiment of this invention. At the start of the experiment, the ball valve 73 was open, thus allowing the flowing gas to reach the sensor 70. The sensor was allowed sufficient time for the output to reach a steady value, before the ball valve 73 was closed, thus isolating the sensor from the flowing test gas. Once the ball valve 73 is closed, the sensor is exposed only to the gas in the sealed volume 77 determined by the sensor 70, sealant 72, tubing 71 and the ball valve 73. From the time when the ball valve 73 was closed, the output from the sensor 70 was followed with time as it decayed to zero output. The recovery time ($T_{90r}$) of the sensor was then determined. The recovery time $T_{90r}$ is the time taken from when the valve 73 was closed to the time when the output from the sensor 70 reached ten percent of its initial steady state response.

The apparatus was calibrated using 40% methane in air from a compressed gas cylinder. The recovery time for methane was determined, and found to be $T_{90r}$=48.5 seconds (average of five measurements).

The experiment was repeated twice, once with test gas B and a second time with test gas C. For test gas B, the $T_{90r}$ recovery time was 118 seconds (average of three measurements) and for test gas C, the $T_{90r}$ recovery time was 12.7 seconds (average of five measurements). The relative diffusion coefficient of the hydrocarbon in test gas B (relative to methane) may be found from the following relationship.

Relative Diffusion Coefficient=($T_{90r}$ for Methane)/($T_{90r}$ for Unknown Gas)

Thus, the relative diffusion coefficient of test gas B compared to methane is 0.41, and the relative diffusion coefficient of test gas C is 3.31. Known values of the relative diffusion coefficients relative to the calibration gas methane, are shown in the table above, in Example 1.

Thus, by comparison of the recovery time for test gas B and test gas C to the ratio recovery time for methane, with the relative diffusion coefficients in the table, test gas B is identified as pentane and test gas C is identified as hydrogen.

Having identified test gas B as pentane and test gas C as hydrogen, the concentrations can be found from the steady state signal. The steady state output of the sensor exposed to 40% LEL methane in air was 45.4 mV. The steady state signal of the sensor exposed to test gas B was 12.1 mV, and since the cross sensitivity ratio for pentane is 50%, the concentration of pentane in test gas A is estimated to be 21% LEL pentane. Similarly the steady state response to the test gas C was 27.3 mV; and since the cross sensitivity ratio for hydrogen is 90%, the concentration of hydrogen in test gas C is estimated to be 27% LEL hydrogen. Test gas B was 0.35% volume (25% LEL) pentane in air from a compressed gas cylinder, and test gas C was 1.0% volume (25% LEL) hydrogen. This example has thus demonstrated that the method described in this disclosure can be used to both identify an unknown gas, and to provide a good estimate the concentration of the gas. These results clearly demonstrate the utility of this method.

EXAMPLE 3

Using the same experimental setup described in Example 1, and shown in FIG. 6, the identity and concentration of a mixture of active gases was measured. At the start of the experiment, the ball valve 73 was open, thus allowing the flowing gas to reach the sensor 70. The sensor was allowed sufficient time for the output to reach a steady value, before the ball valve 73 was closed, thus isolating the sensor from the flowing test gas. Once the ball valve 73 was closed, the sensor was exposed only to the gas in the sealed volume 77 determined by the sensor 70, sealant 72, tubing 71 and the ball valve 73. From the time when the ball valve 73 was closed, the output from the sensor 70 was followed with time as it decayed to zero output. The output of the sensor was recorded as a function of time as the output signal decayed. The apparatus was calibrated using 25% butane in air from a compressed gas cylinder, (average of four measurements). The response of the sensor to the calibration gas, 25% LEL butane was 16.2 mV.

A test gas mixture D was applied to the sensor and the sensor output signal at 5, 10, 20 and 30 seconds was recorded. Test gas D contained two active components. The sensor response at each of these times was calculated using the double exponential function:

$$\text{Sensor response}=W\exp(-Xt)+Y\exp(-Zt)$$

and the difference between the experimental value and the calculated value was minimized by adjusting the parameters W, X, Y and Z. The minimization was done using the 'Solver' function in Microsoft Corporation's Excel 97.
The results from this fit were as follows:

$$W=11.9\ mV\ X=0.031\ s^{-1}$$

$$Y=12.8\ mV\ Z=0.057\ s^{-1}$$

The response of the sensor is measured as a potential, thus the units of W and Y are in mV. By comparing the ratio of X and Y to that obtained for the butane by fitting a single exponential to the entire decay curve ($0.035\ s^{-1}$), the relative diffusion coefficients are $D_X=0.89$ and $D_Y=1.6$. The gases are identified by comparison to the relative diffusion coefficients in Table 2 as pentane and methane for X and Y respectively. The cross sensitivity of these two gases are 1.0 for methane, 0.50 for pentane and 0.60 for butane (Product Data Handbook, vol. 1, Safety, issue 4.0, January 1997, City Technology Ltd., Portsmouth, United Kingdom). Therefore, the concentration of the methane and the pentane components of the unknown test gas can be determined from the following relationship:

$$\text{Concentration}=(R_{gas}/R_{butane})\ (XS_{butane}/XS_{gas})\ (\text{Concentration butane})$$

wherein $R_{gas}$ is the response to the component of the test gas (i.e. W or Y) and $R_{butane}$ is the response to butane, $XS_{butane}$ and $XS_{gas}$ are the cross sensitivities of the sensor to butane and the active component of the gas mixture (i.e. methane or pentane).

Thus, the methane concentration in the gas mixture was 12% LEL and the concentration of pentane was 22% LEL. The nominal composition of the unknown test gas mixture was 17% LEL each of pentane and methane in air. Thus it has been demonstrated that it is possible to take a mixture of gases and identify the active components of the mixture and to measure the concentrations of each component. These results clearly demonstrate the utility of this method.

What is claimed is:

1. A method for identifying at least one component of an unknown gas mixture using a diffusion limited sensor providing an electrical signal output response when exposed to the gas mixture, comprising the steps of:

disposing the sensor in a chamber of fixed volume and having a gas input and gas output through which the gas flows, diffusion limiting means being disposed between the chamber and an inlet to the sensor;

connecting the chamber to a source of a known test gas of known concentration and known diffusion coefficient, opening the input to the chamber, and causing the sensor to be exposed to the known test gas, and recording the response of the sensor at at least one time prior to and until a steady state electrical signal output response from the sensor is obtained;

closing the input to the chamber and disconnecting the chamber from the source of the known test gas;

connecting the chamber to a source of said unknown gas mixture;

opening the input to the chamber and exposing the sensor to a flow of unknown gas mixture and recording the response of the sensor at at least one time prior to and until a steady state electrical signal output response from the sensor is obtained;

calculating a diffusion coefficient and concentration for reactive components of the unknown gas mixture by comparison of the response of the sensor to the unknown gas mixture to the response to the known gas;

mathematically modeling the response of the sensor to at least one component of the unknown gas mixture; and identifying the at least one component of the unknown gas mixture.

2. The method of claim 1, wherein the sensor is an electrochemical sensor.

3. The method of claim 1, wherein the sensor is a catalytic bead sensor.

4. A method for identifying at least one unknown component of an unknown gas mixture using a diffusion limited sensor providing an electrical signal output response when exposed to the gas mixture, comprising the steps of:

disposing the sensor in a chamber of fixed volume and having a gas input and gas output through which the gas flows, diffusion limiting means being disposed between the chamber and an inlet to the sensor;

connecting the chamber to a source of a known test gas of known concentration and known diffusion coefficient, opening the input to the chamber, and causing the sensor to be exposed to the known test gas until a steady state electrical signal output response from the sensor is obtained, then closing the input to the chamber and recording the response of the sensor at at least one time prior to and until a steady state electrical signal output from the sensor is obtained;

closing the input to the chamber and disconnecting the chamber from the source of the known test gas;

connecting the chamber to a source of said unknown gas mixture;

opening the input to the chamber and exposing the sensor to a flow of unknown gas mixture until a steady state response is obtained, then closing the input to the chamber and recording the response of the sensor at at least one time prior to and until a steady state electrical signal output response from the sensor is obtained;

calculating diffusion coefficients and concentrations for reactive components of the unknown gas mixture by comparison of the response of the sensor to the unknown gas mixture to the response to the known gas;

mathematically modeling the response of the sensor to at least one component of the unknown gas mixture; and identifying the at least one unknown component of the unknown gas mixture.

5. The method of claim 4, wherein the sensor is an electrochemical sensor.

6. The method of claim 4, wherein the sensor is a catalytic bead sensor.

7. A method of determining if an unknown gas mixture contains one or more reactive components, using a diffusion limited sensor providing an electrical signal output response when exposed to the gas mixture, comprising the steps of:

disposing the sensor in a chamber of fixed volume and having a gas input and gas output through which the gas flows, diffusion limiting means being disposed between the chamber and an inlet to the sensor;

connecting the chamber to a source of a known test gas of known concentration and known diffusion coefficient, opening the input to the chamber, and causing the sensor to be exposed to the known test gas, and recording the response of the sensor at at least one time prior to and until a steady state electrical signal output response from the sensor is obtained;

closing the input to the chamber and disconnecting the chamber from the source of the known test gas;

connecting the chamber to a source of said unknown gas mixture;

opening the input to the chamber and exposing the sensor to a flow of unknown gas mixture, and recording the response of the sensor at at least one time prior to and until a steady state response is obtained;

comparing the response of the sensor to the unknown gas mixture to the response to the known gas, and calculating a ratio of unknown gas mixture to known gas response, said ratio either being time required to until the response reaches a given fraction of the steady state response or change in response at a given time after opening the input to the chamber; and identifying the at least one component of the unknown gas mixture from constancy or variation in said ratio.

8. The method of claim 7, wherein the sensor is an electrochemical sensor.

9. The method of claim 7, wherein the sensor is a catalytic bead sensor.

10. A method of determining if an unknown gas mixture contains one or more unknown reactive components, using a diffusion limited sensor providing an electrical signal output response when exposed to the gas mixture, comprising the steps of:

disposing the sensor in a chamber of fixed volume and having a gas input and gas output through which the gas flows, diffusion limiting means being disposed between the chamber and an inlet to the sensor;

connecting the chamber to a source of a known test gas of known concentration and known diffusion coefficient, opening the input to the chamber, and causing the sensor to be exposed to the known test gas until an initial steady state electrical signal output response from the sensor is obtained, then closing the input to the chamber and recording the response of the sensor at at least one time prior to an until a final steady state electrical signal output from the sensor is obtained;

closing the input to the chamber, disconnecting the chamber from the source of the known test gas;

connecting the chamber to a source of said unknown gas mixture;

opening the input to the chamber and exposing the sensor to a flow of unknown gas mixture until an initial steady state response is obtained, then closing the input to the chamber and recording the response of the sensor at at least one time prior to and until a final steady state electrical signal output response from the sensor is obtained;

comparing the response of the sensor to the unknown gas mixture to the response to the known gas, and calculating a ratio of unknown gas mixture response to known gas response, said ratio either being time required until the response reaches a given fraction of the final steady state response or change in response at a given time after closing the input to the chamber after the initial steady state response; and identifying the at least one unknown component of the unknown gas mixture from constancy or variation in said ratio.

11. The method of claim 10, wherein the sensor is an electrochemical sensor.

12. The method of claim 10, wherein the sensor is a catalytic bead sensor.

13. A method of identifying at least one component of an unknown gas or gas mixture, using a diffusion limited sensor providing an electrical signal output response when exposed to the unknown gas or mixture, comprising the steps of:

disposing the sensor in a chamber of fixed volume and having a gas input and gas output through which the gas flows, diffusion limiting means being disposed between the chamber and an inlet to the sensor;

connecting the chamber to a source of a known test gas of known concentration and known diffusion coefficient, opening the input to the chamber, and causing the sensor to be exposed to the known test gas, and recording the response of the sensor at at least one time prior to and until a steady state electrical signal output response from the sensor is obtained;

closing the input to the chamber and disconnecting the chamber from the source of the known test gas;

connecting the chamber to a source of said unknown gas mixture;

opening the input to the chamber and exposing the sensor to a flow of unknown gas or gas mixture and recording the response of the sensor at at least one time prior to and until a steady state electrical signal output response from the sensor is obtained;

comparing times of response for the unknown gas or gas mixture with the response times for the known gas to determine whether the unknown gas or mixture is a single gas or a gas mixture;

if the unknown gas or mixture is a single gas, calculating the diffusion coefficient thereof from the diffusion coefficient of the known gas and the times of response for the known gas and the unknown single gas; and if the unknown gas or gas mixture is a gas mixture, fitting a mathematical model to the sensor response, calculating diffusion coefficients and concentrations for the components of the unknown gas mixture, and identifying the components of the unknown gas mixture.

14. The method of claim 13, wherein the sensor response for the known test gas and unknown gas or mixture is time necessary to obtain a predetermined percentage of steady state output.

15. The method of claim 13, additionally comprising closing the input to the sensor after the steady state output is achieved for the known test gas and the unknown gas or gas mixture, wherein the sensor response is time necessary to attain a predetermined percentage of steady state output after the input to the sensor is closed.

* * * * *